United States Patent [19]
Wang et al.

[11] Patent Number: 5,831,116
[45] Date of Patent: Nov. 3, 1998

[54] CATALYTIC PROCESS FOR MAKING ETHERS, ALDEHYDES ESTERS AND ACIDS FROM ALCOHOLS USING A SUPERCRITICAL FLUID MOBILE

[75] Inventors: Chien-Tsung Wang, Arlington; Ronald J. Willey, Dedham, both of Mass.

[73] Assignee: Northeastern University, Boston, Mass.

[21] Appl. No.: 844,438

[22] Filed: Apr. 18, 1997

Related U.S. Application Data

[60] Provisional application No. 60/033,186, Dec. 18, 1996.

[51] Int. Cl.$^6$ ..................................................... C07C 67/00

[52] U.S. Cl. .......................... 560/239; 568/698; 568/431; 560/231; 562/538; 562/539

[58] Field of Search ..................................... 568/698, 431; 560/239, 231; 562/538, 539

[56] References Cited

U.S. PATENT DOCUMENTS

| | | | |
|---|---|---|---|
| 4,177,167 | 12/1979 | Manara et al. | 252/455 |
| 4,337,366 | 6/1982 | Fattore et al. | 568/698 |

OTHER PUBLICATIONS

Lubo Zhou and Aydin Akgerman: Ind. Eng. Chem. Res. Jan. 5, 1995, 34, 1588–1595.

*Primary Examiner*—Gary Geist
*Assistant Examiner*—J. Parsa
*Attorney, Agent, or Firm*—Weingarten, Schurgin, Gagnebin & Hayes LLP

[57] ABSTRACT

A process for partially oxidizing alcohols such as methanol, comprising the steps of a) introducing into a reactor unit containing a solid acid catalyst amounts of alcohol and oxygen; and a supercritical fluid (such as SCF $CO_2$) mobile phase; and b) partially oxidizing the alcohol to its corresponding ether, aldehyde, ester or acid. In an advantageous embodiment, methanol is oxidized using an aerogel acid catalyst to produce methyl ether.

5 Claims, 13 Drawing Sheets

FIG. 1

Flow Diagram for Supercritical Fluid Reactor System

FIG. 2
Methanol Oxidation in Supercritical Carbon Dioxide
1 wt% Fe₂O₃/SiO₂ Catalyst

FIG. 3

Methanol Oxidation in Supercritical Carbon Dioxide
10 wt% $Fe_2O_3/SiO_2$ Catalyst

FIG. 4

Methanol Oxidation in Supercritical Carbon Dioxide
20 wt% Fe$_2$O$_3$/SiO$_2$ Catalyst

FIG. 5

Methanol Oxidation in Supercritical Carbon Dioxide
Fe₂O₃ Catalyst

FIG. 6

Methanol Oxidation in Supercritical Carbon Dioxide
20 wt% $Fe_2O_3/MoO_3$ Catalyst

FIG. 7
Methanol Oxidation in Supercritical Carbon Dioxide
1 wt% Fe$_2$O$_3$/SiO$_2$ Catalyst

FIG. 8
Methanol Oxidation in Supercritical Carbon Dioxide
10 wt% $Fe_2O_3/SiO_2$ Catalyst

FIG. 9 Methanol Oxidation in Supercritical Carbon Dioxide
20 wt% Fe₂O₃/SiO₂ Catalyst

FIG. 10
Methanol Oxidation in Supercritical Carbon Dioxide
Fe₂O₃ Catalyst

*FIG. 11*
Methanol Oxidation in Supercritical Carbon Dioxide
20 wt%Fe$_2$O$_3$/MoO$_3$ Catalyst

FIG. 12

Effects of Reactant Concentrations on Production Rates for Methanol Oxidation in Supercritical Carbon Dioxide
$Fe_2O_3$ Catalyst FIG. 13  Comparison of Activity and Production Rates from Methanol Oxidation in Supercritical $CO_2$ and Gaseous CO $Fe_2O_3$ Catalyst

5,831,116

CATALYTIC PROCESS FOR MAKING ETHERS, ALDEHYDES ESTERS AND ACIDS FROM ALCOHOLS USING A SUPERCRITICAL FLUID MOBILE

CROSS-REFERENCE TO RELATED APPLICATIONS

The instant invention claims priority of co-pending and commonly-assigned Provisional Patent Application No. 60/033,186, filed Dec. 18, 1996.

FIELD OF THE INVENTION

This invention relates generally to methods for dehydrating, or partially oxidizing alcohols to ethers, aldehydes, esters or acids, and particularly towards catalytic methods of producing ethers, aldehydes, esters or acids from alcohols, employing supercritical fluids.

BACKGROUND OF THE INVENTION

It is well-known that alcohols such as methanol can be dehydrated with strong acid and high reaction temperatures produce ethers, e.g., dehydrating methanol to produce methyl ether:

However, these conventional methods are made less desirable because of the corrosion of the reactor caused by the use of strong acid; the harsh reaction conditions; and the necessity of having to recover the acid.

Methyl ether, $CH_3OCH_3$, has been suggested as a suitable replacement for chlorofluorocarbons, e.g., Freon®, in cleaning applications. However, the cost of methyl ether (as of September 1996), about $0.56/lb, is disadvantageously high for use in such applications. As such, a comparatively cleaner, more efficient and cheaper method of making low molecular weight organic compounds with high commercial value (e.g., ethers, aldehydes, esters and acids such as dimethyl ether, formaldehyde, methyl formate and formic acid) from alcohols, preferably primary alcohols such as methanol, has long been desired.

BRIEF SUMMARY OF THE INVENTION

A process for partially oxidizing alcohols such as methanol is disclosed, comprising the steps of a) introducing into a reactor unit containing a bed of solid acid catalyst, amounts of alcohol and oxygen; and a supercritical fluid ("SCF") (such as SCF $CO_2$) mobile phase; and b) partially oxidizing the alcohol to its corresponding ether, aldehyde, ester or acid, wherein the operating pressure and temperature is greater than the critical point pressure and temperature of mixture of alcohol, oxygen and SCF. In an advantageous embodiment, methanol is partially oxidized using an aerogel acid catalyst to produce methyl ether, formaldehyde, methyl formate, or formic acid.

BRIEF DESCRIPTION OF THE DRAWINGS

The invention will be more fully understood by reference to the following Detailed Description Of The Invention in conjunction with the following Drawings, of which.

DETAILED DESCRIPTION OF THE INVENTION

Supercritical fluids ("SCFs") have gas and liquid-like characteristics and their physicochemical properties such as density, mass transfer coefficient, and viscosity are between gas and liquid phases. SCFs also offer a convenient means of salvation due to the ability to adjust pressure and temperature of the SCF without adversely affecting the chemical structure of the chemical components dissolved in the SCF.

The inventors have discovered that alcohols such as primary alcohols may be partially oxidized in SCFs such as SCF $CO_2$ to produce the corresponding ether, aldehyde, ester or acid. The process involves introduction of amounts of the alcohol and oxygen into a reactor unit (which may be, e.g., a fixed bed or fluidized bed reactor) containing a solid acid catalyst using a SCF mobile phase, and partially oxidizing the alcohol to its corresponding ether, aldehyde, ester or acid. The catalyst advantageously comprises a solid acid catalyst.

In an advantageous embodiment, methanol may be partially oxidized to produce ethers, aldehydes, esters or acids of methanol, such as dimethyl ether, formaldehyde, methyl formate and formic acid.

The ratio of oxygen to alcohol in the system is desirably in the range of about 0.6:1 to 2.5:1.

The catalyst used in the disclosed process has 1) redox functionality, and 2) Lewis acid site(s) and/or Bronsted acid sites that can attract the reactant molecules, i.e., they adsorb the reactant (alcohol), and interact with oxygen. In one embodiment the catalyst is advantageously a solid acid catalyst like a transition metal oxide or combination thereof, particularly when on a support like silica, alumina, zirconia or $TiO_2$. (Silica and alumina alone may also be used as catalysts.) Transition metal oxides which may be used are oxides of metals from Groups IVB, VB, VIB, VIII, and IB, particularly the Group VIII metals. Exemplary oxides are those of Ti, Zr, V, Cr, Mn, Fe, Co, Cr, Ni, and Cu, particularly Fe, Mo, Ni, V, and Ti. Combinations or mixed metal oxides may be used. Examples of suitable acid catalysts are $Fe_2O_3/SiO_2$ (i.e., iron oxide on silica), $Fe_2O_3/Al_2O_3$, $Fe_2O_3/TiO_2$, $Cr_2O_3/Al_2O_3$, $Cr_2O_3/SiO_2$, $Cr_2O_3/TiO_2$, $V_2O_5/SiO_2$, $V_2O_5/Al_2O_3$, $V_2O_5/TiO_2$, $NiO/Al_2O_3$, $NiO/SiO_2$, and $NiO/TiO_2$. In a preferred embodiment an aerogel catalyst, such as described in the Example, is used. Such aerogel catalysts may be prepared by conventional sol-gel methods through a high temperature supercritical drying process. Iron oxide is advantageous because of its low cost and particular suitability for the purpose, e.g., its relative acidity.

The preferred SCF is SCF $CO_2$, although SCF $N_2$ may be used as well.

The disclosed partial oxidation process is carried out under SCF pressure and temperature conditions. The desired pressure range is about 1200 to 1800 psig and the reaction temperature range is desirably about 200°–330°C., preferably 225°–300° C. The catalyst is desirably pretreated in SCF $CO_2$ with a small flow rate of oxygen at 450° C. for 2 hours. Regeneration may be done in the same manner as pretreatment. The optimum operating pressure and temperature chosen for a particular process will depend on, e.g., the catalyst and reactants used, but in any event should at least be greater than the critical point pressure and temperature of the mixture of alcohol, oxygen and SCF. It has been found that the higher system temperature the higher probability that the oxidation reaction shifts to totality, i.e., oxidation to $CO_2$.

For safety considerations, the total oxygen concentration (TOC) in the system should be less than the minimum oxygen concentration (MOC), in order to avoid explosion or combustion.

The disclosed process has several distinct and unexpected advantages. Firstly, the partial oxidation reaction occurs under much milder reaction conditions than conventional reactions, i.e., no strong acid or high temperature is required (a consideration for extraction of thermally sensitive materials.) Secondly, use of an SCF mobile phase has been surprisingly found to extend the life of the catalyst because catalyst poisoning due to carbon deposition is reduced, an attractive feature to today's cost-conscious chemical industry. Thirdly, use of an SCF mobile phase enables the process chemist to manipulate solute solubility, density, diffusion coefficient, reaction rate, yield and selectivity.

Figure 1:
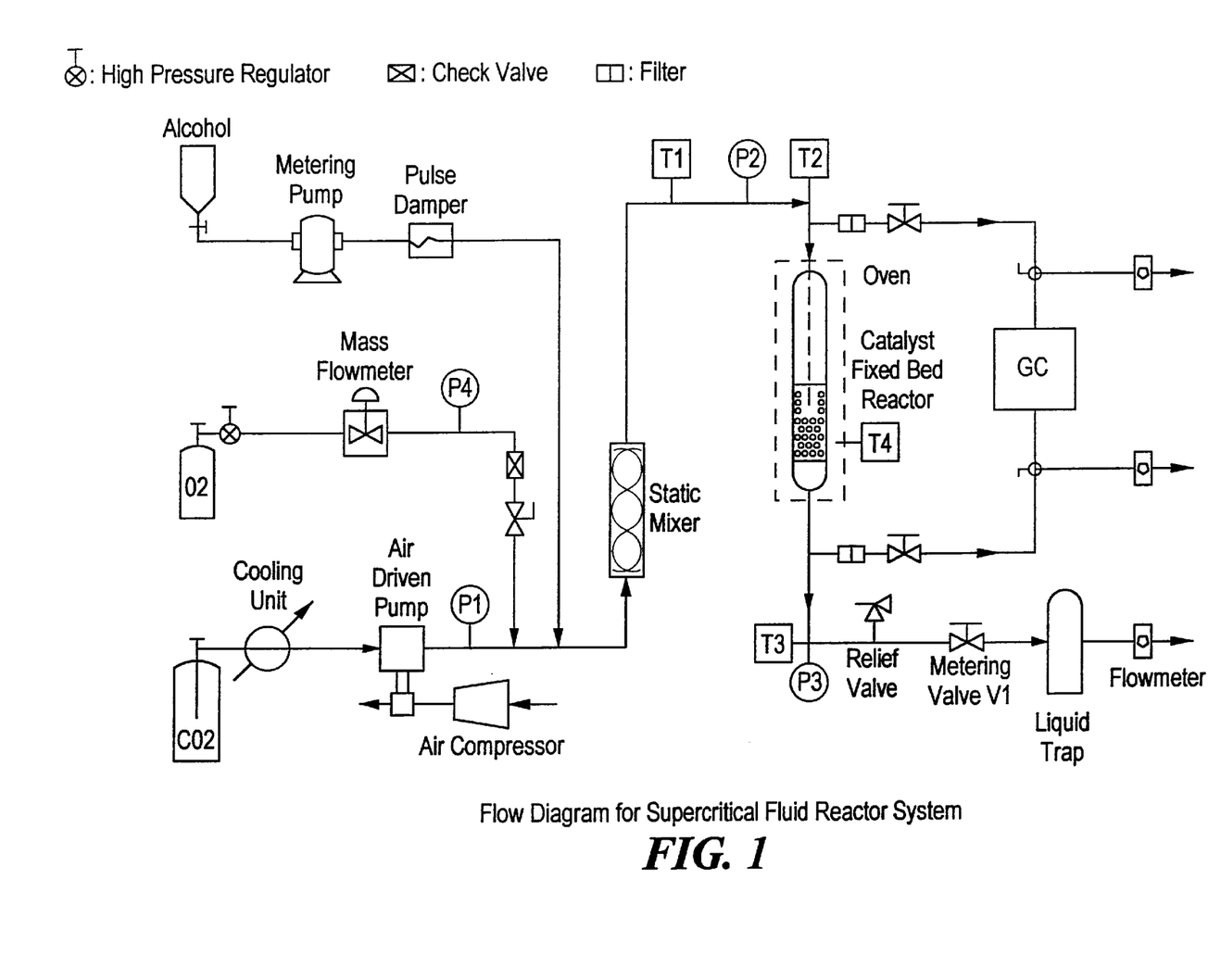
FIG. 1 illustrates a process for partially oxidizing simple alcohols such as methanol in accordance with the disclosure.

FIG. 1 schematically illustrates a system on which the disclosed process is advantageously carried out. The supercritical fluid reactor system is composed of six major parts: the reactant supply, the pumping system, the mixer, the heating system, the catalytic reactor unit, and the analysis system (i.e., gas chromatograph.)

EXAMPLES

To demonstrate the disclosed process, several pure and mixed oxide aerogel catalysts were prepared for use in the catalytic partial oxidation of methanol in supercritical carbon dioxide, as illustrated in Table I:

Table I 1. 1 wt % iron oxide/silica ($Fe_2O_3/SiO_2$)
2. 5 wt % iron oxide/silica ($Fe_2O_3/SiO_2$)
3. 10 wt % iron oxide/silica ($Fe_2O_3/SiO_2$)
4. 20 wt % iron oxide/silica ($Fe_2O_3/SiO_2$)
5. Iron oxide ($Fe_2O_3$)
6. 20 wt % iron oxide/molybdenum oxide ($Fe_2O_3/MoO_3$)

The aerogel catalysts were prepared by the sol-gel method through a high temperature supercritical drying process. The process used to prepare the 20 wt % $Fe_2O_3/SiO_2$ aerogel (co-gel procedure) is exemplary and is detailed below.

Two separate solutions were prepared according to a selected oxide mass concentration. Solution 1 contained ferric acetylacetonate in methanol, and solution 2 contained tetramethyl orthosilicate in methanol. Solution 2 was rapidly stirred, and solution 1 was slowly poured into solution 2. Water was then added into the mixing solution at 1.4 times the stoichiometric amount required for hydrolyzing both precursors to their relevant hydroxides. A mixed oxide gel formed with gelatin after mixing for 10 minutes. Complete reaction and mixing were attained by continuous stirring for 1 hour. The final gel solution was then placed into a Pyrex glass liner which was then placed in an autoclave.

The autoclave was then heated at about 2°–3° C./min in order to perform supercritical drying effectively. The pressure in the closed system increased with the increasing temperature, and the process temperature and pressure followed the solvent (methanol) vapor-liquid equilibrium line. The critical properties of methanol were used to determine the termination point. After reaching the supercritical region, the pressure was then slowly released maintaining at a constant temperature. Finally, the autoclave was purged with a nitrogen flow and cooled to room temperature. The resulting aerogel with hydrocarbon residues was then removed from the autoclave, calcined at 723 K (450° C.) in an oven, and stored in a glass jar before use.

An integral catalyst fixed-bed reactor was used in a system illustrated in FIG. 1. Conversion versus temperature profiles at constant mass space velocities (mass flow rate of $CO_2$ kept constant as temperature was changed inside the reactor) were obtained. The total feed rate of the mixture was 7.2 g/min (0.16 gmol/min). The methanol/oxygen/$CO_2$ ratio was 1.5:2.5:96 (mol %). The mass of catalyst in the reactor was 1.5 g; system pressure was 1300 psig. Each catalyst was tested for three runs for determining stability. Three steady state conversion data were measured at each temperature. The steady state was assumed based upon 45 minutes of reaction time for each constant temperature. Catalyst was pretreated and regenerated in small flow rate of oxygen at 450° C. for 2 hours.

Figure 2:
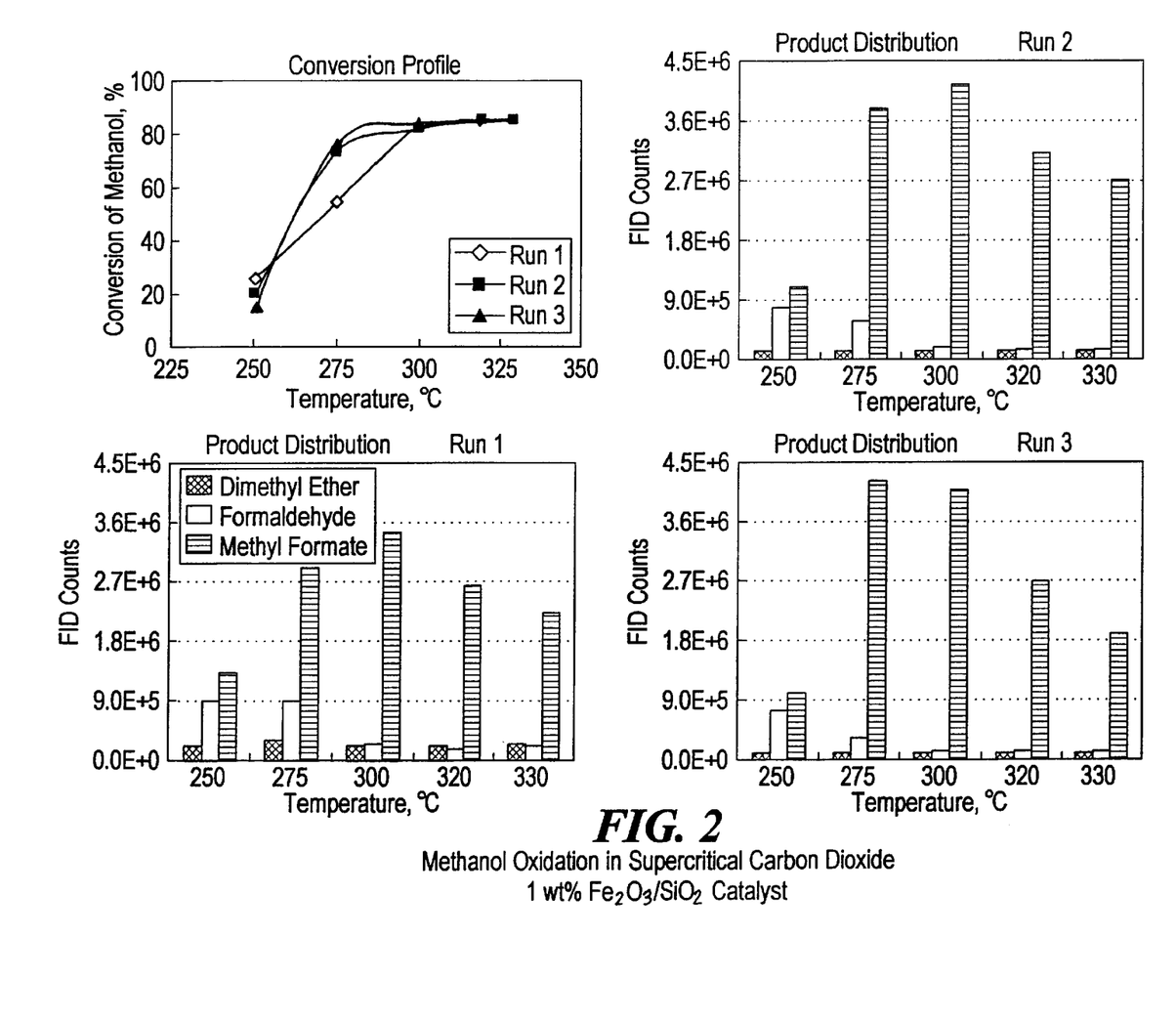
FIGS. 2–13 are graphical depictions of experimental data more particularly described in the Example.
Figure 3:
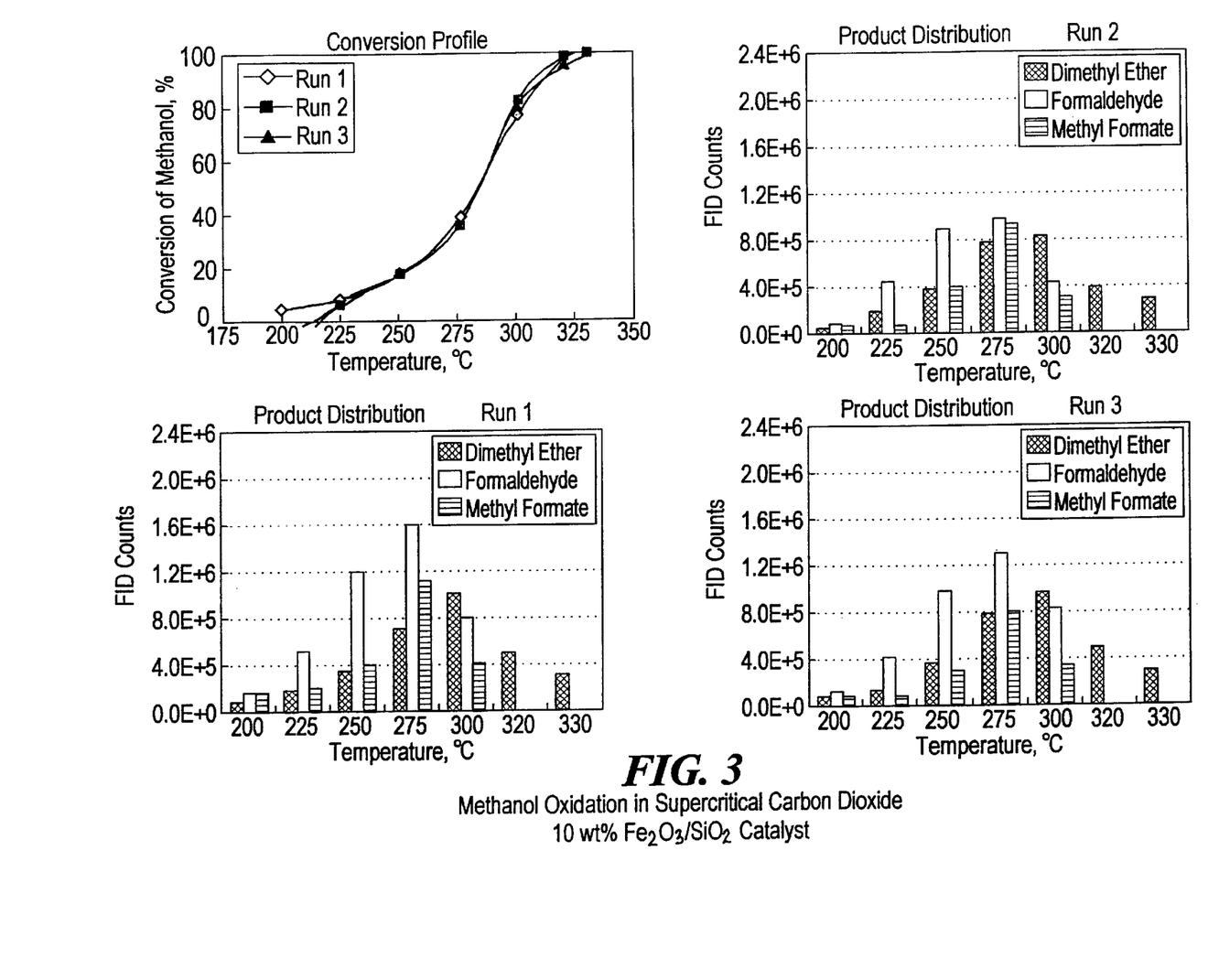
Figure 4:
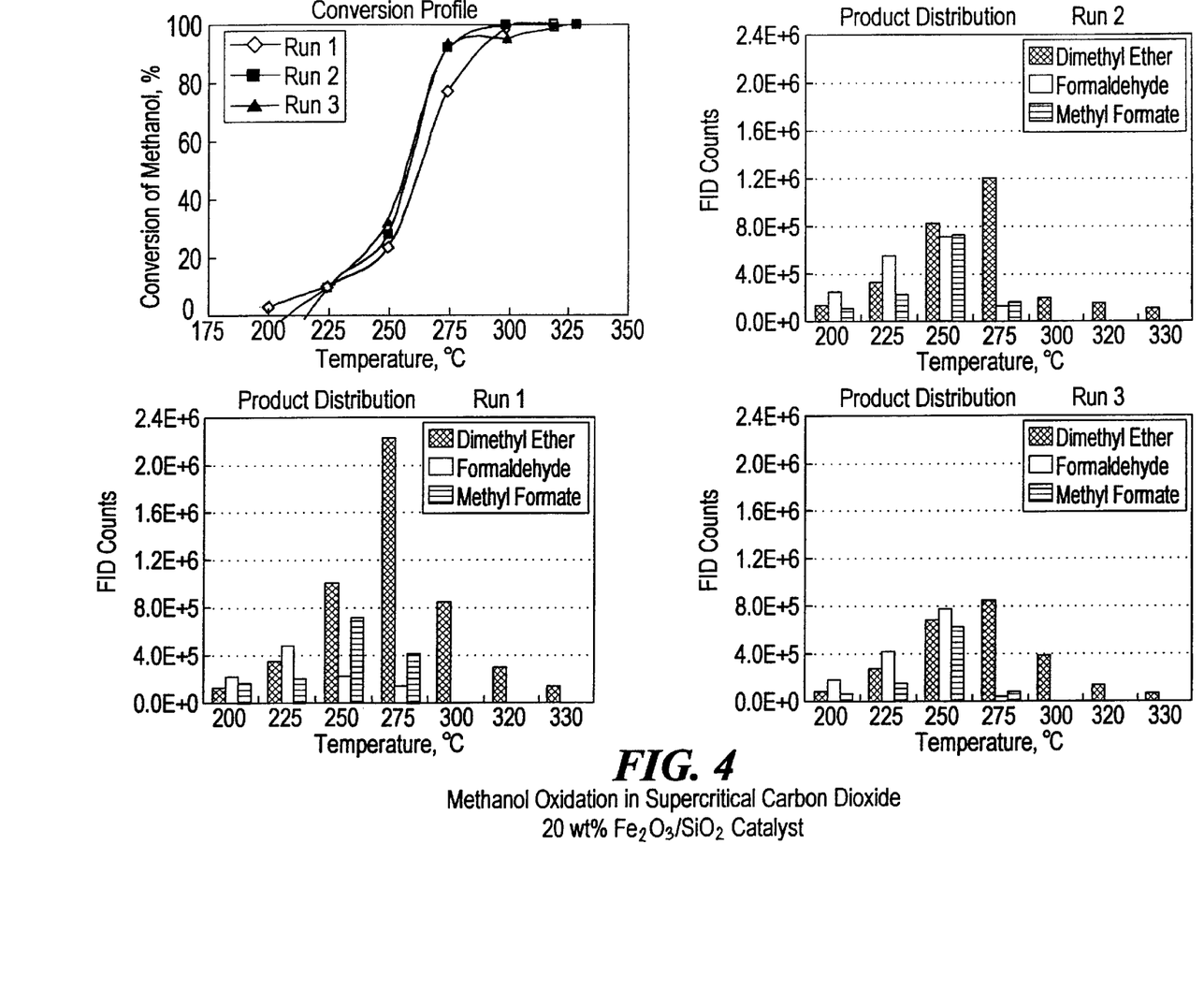
Figure 5:
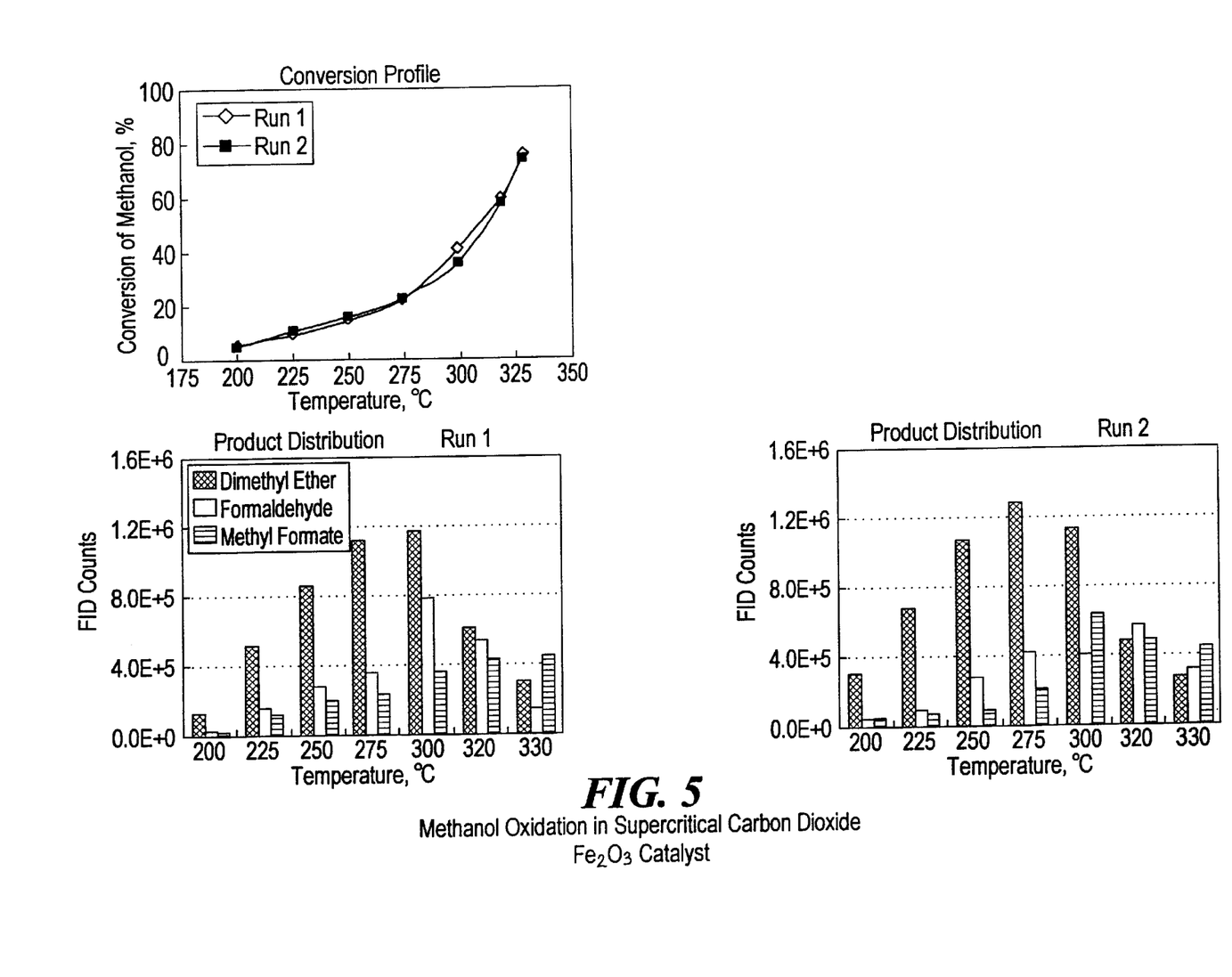
Figure 6:
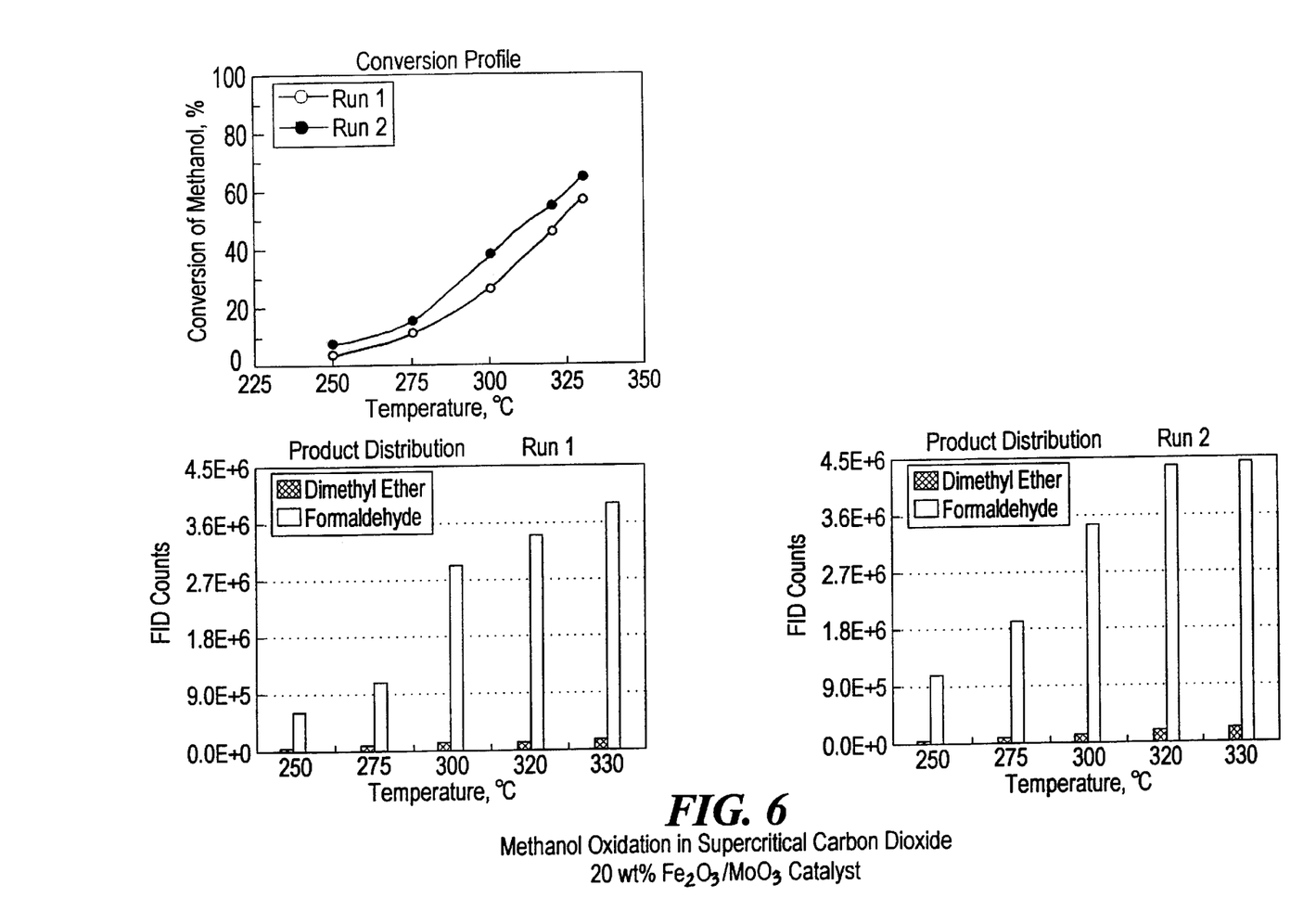
Figure 7:
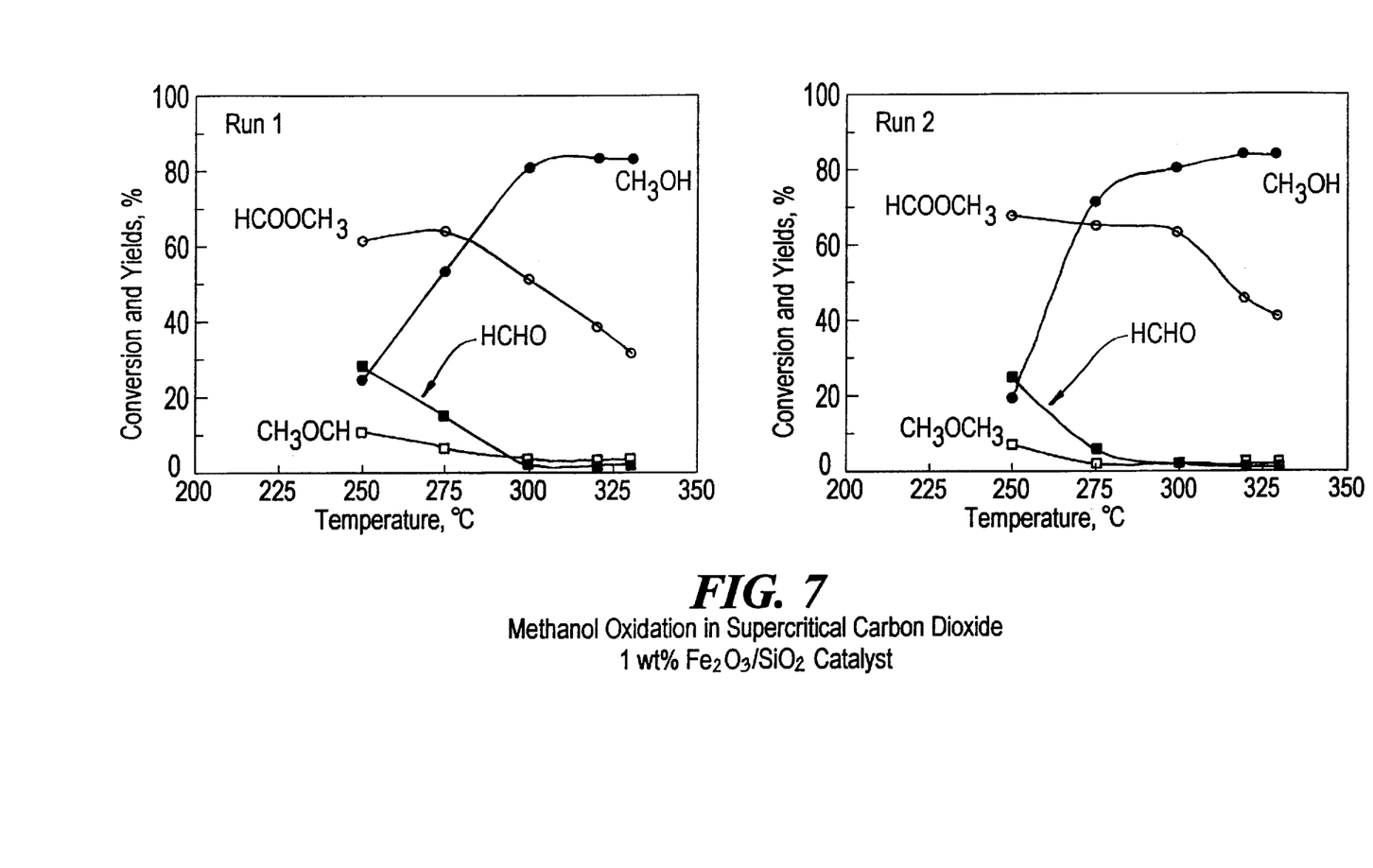
Figure 8:
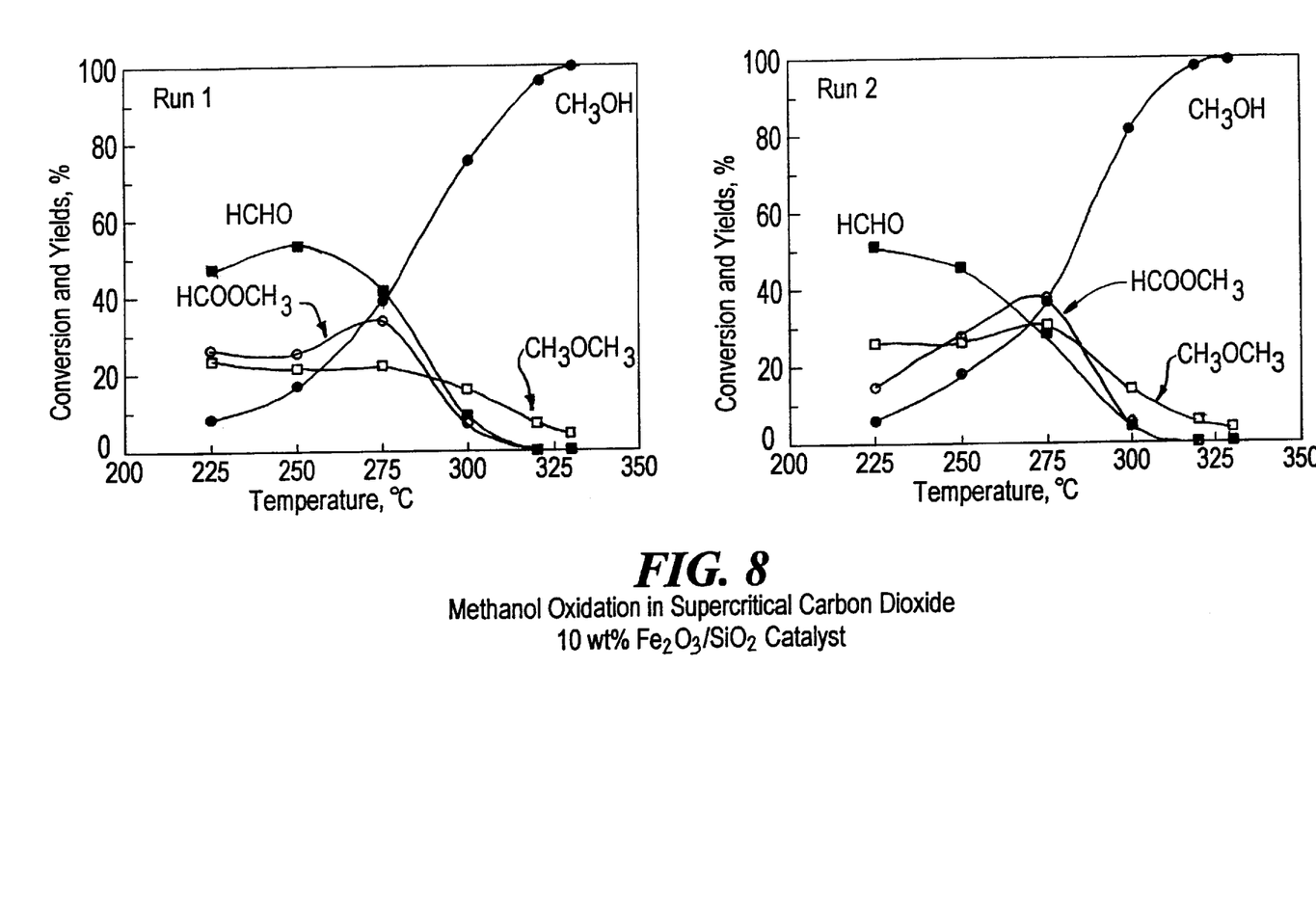
Figure 9:
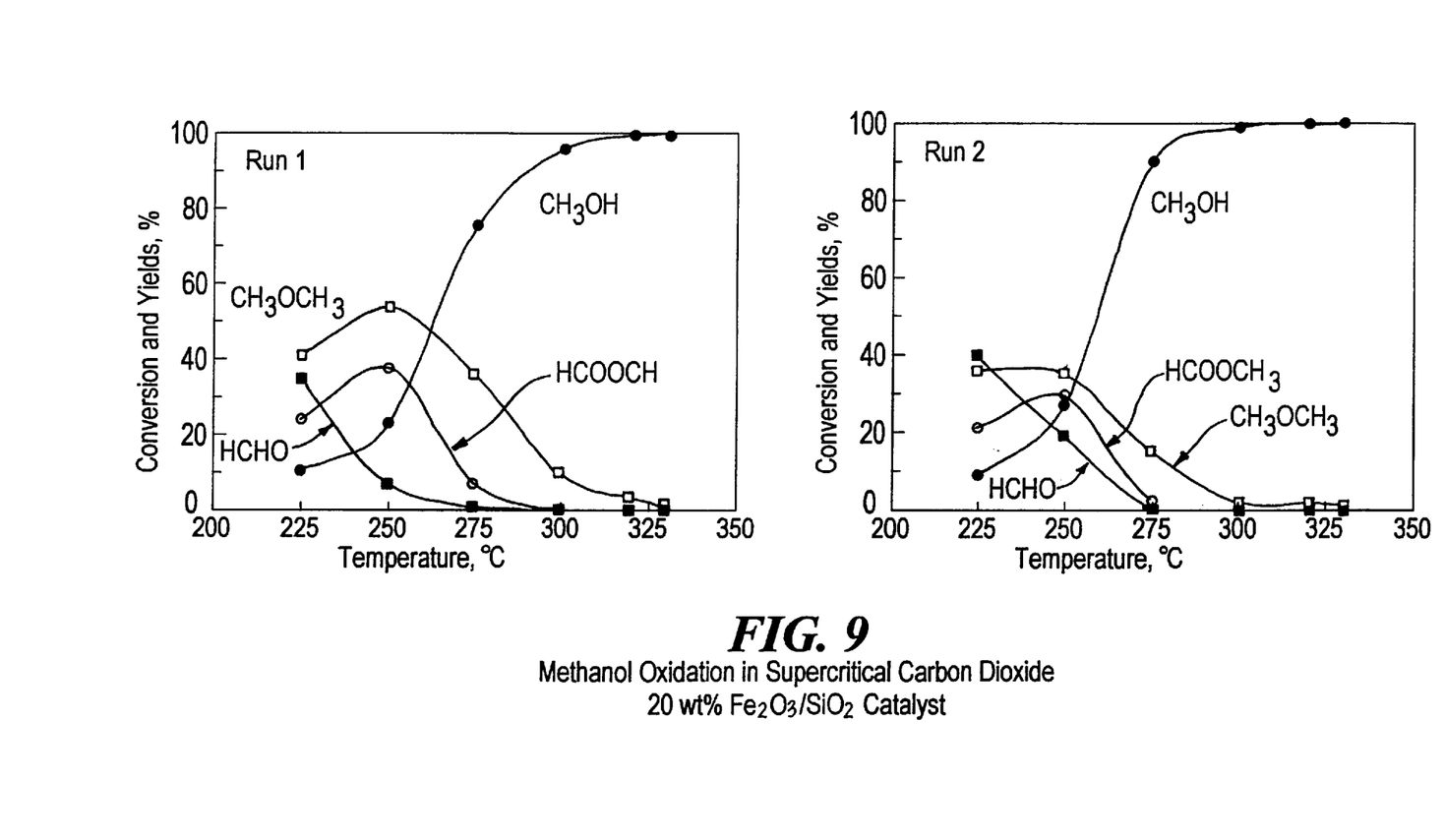
Figure 10:
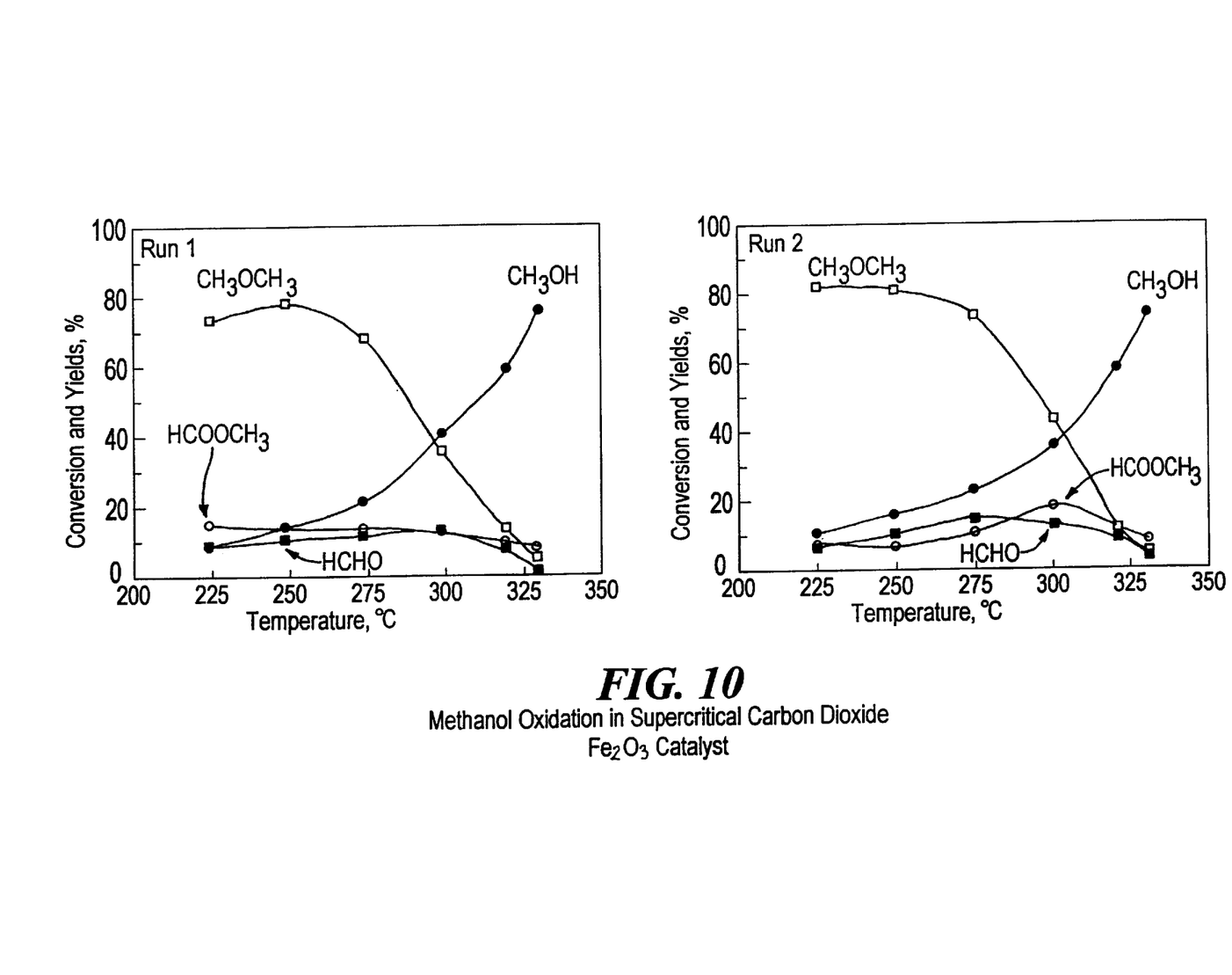
Figure 11:
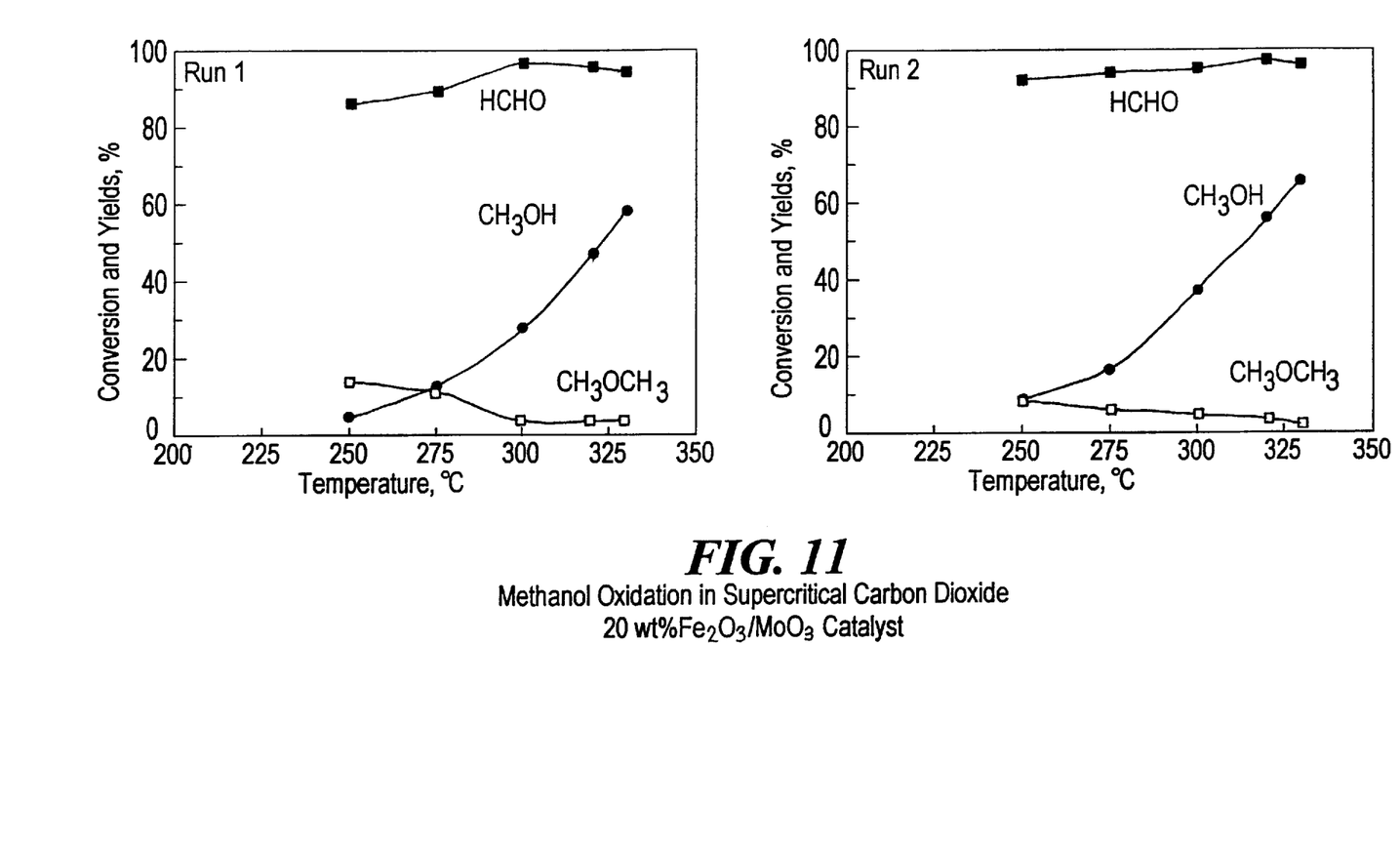

The data are presented as conversion profiles and product distribution profiles versus temperature in FIGS. 2–13, which are identified as follows:

FIG. 2: conversion profiles and product distribution profiles versus temperature, $Fe_2O_3/SiO_2=1/99$ FIG. 3: conversion profiles and product distribution profiles versus temperature, $Fe_2O_3/SiO_2=10/90$ FIG. 4: conversion profiles and product distribution profiles versus temperature, $Fe_2O_3/SiO_2=20/80$ FIG. 5: conversion profiles and product distribution profiles versus temperature, $Fe_2O_3$ FIG. 6: conversion profiles and product distribution profiles versus temperature, $Fe_2O_3/MoO_3=20/80$ FIG. 7: Methanol conversion and individual product yields versus temperature, $Fe_2O_3/SiO_2=1/99$ FIG. 8: Methanol conversion and individual product yields versus temperature, $Fe_2O_3/SiO_2=10/90$ FIG. 9: Methanol conversion and individual product yields versus temperature, $Fe_2O_3/SiO_2=20/80$ FIG. 10: Methanol conversion and individual product yields versus temperature, $Fe_2O_3$ FIG. 11: Methanol conversion and individual product yields versus temperature, $Fe_2O_3/MoO_3=20/80$

Figure 12:
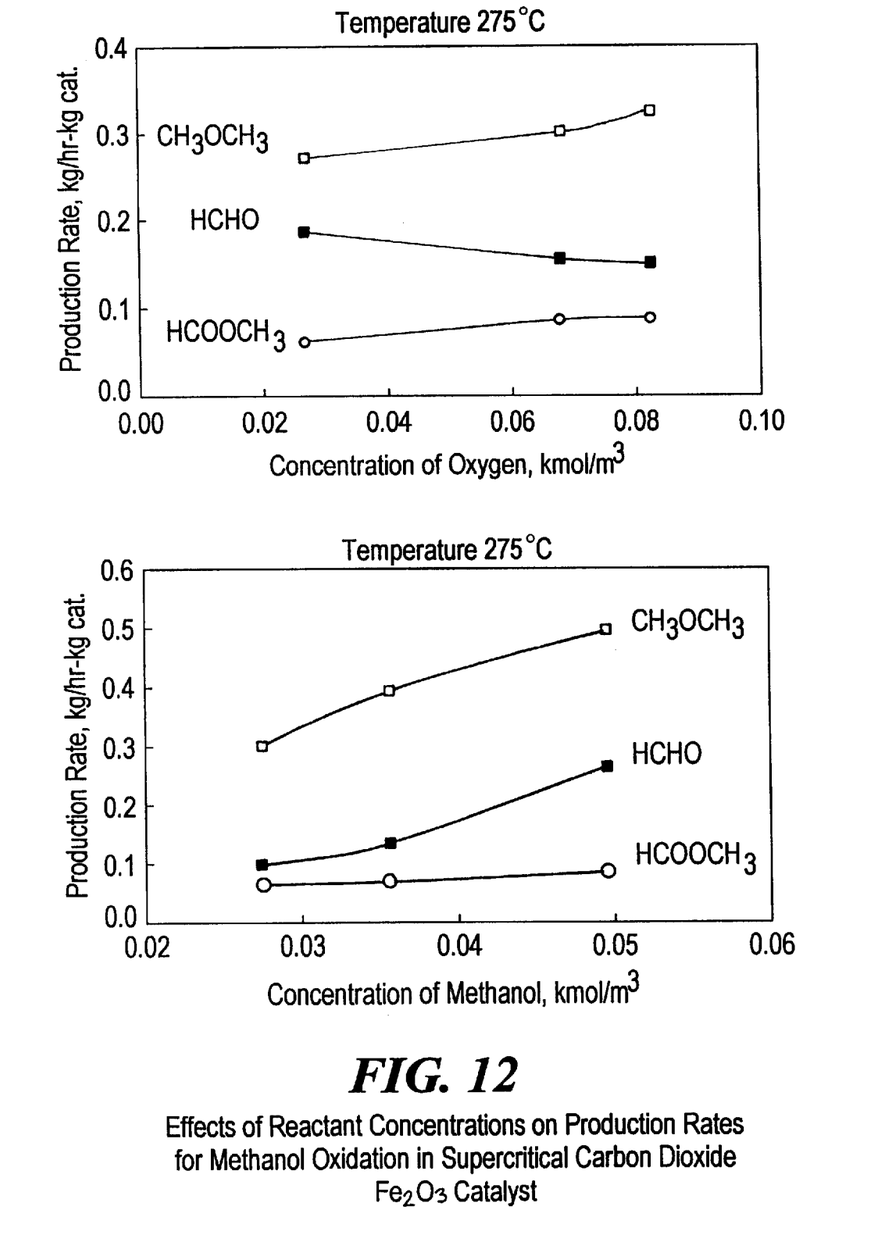

FIG. 12: Effect of reactant concentration on production rate over $Fe_2O_3$ catalyst at 275° C.

Figure 13:
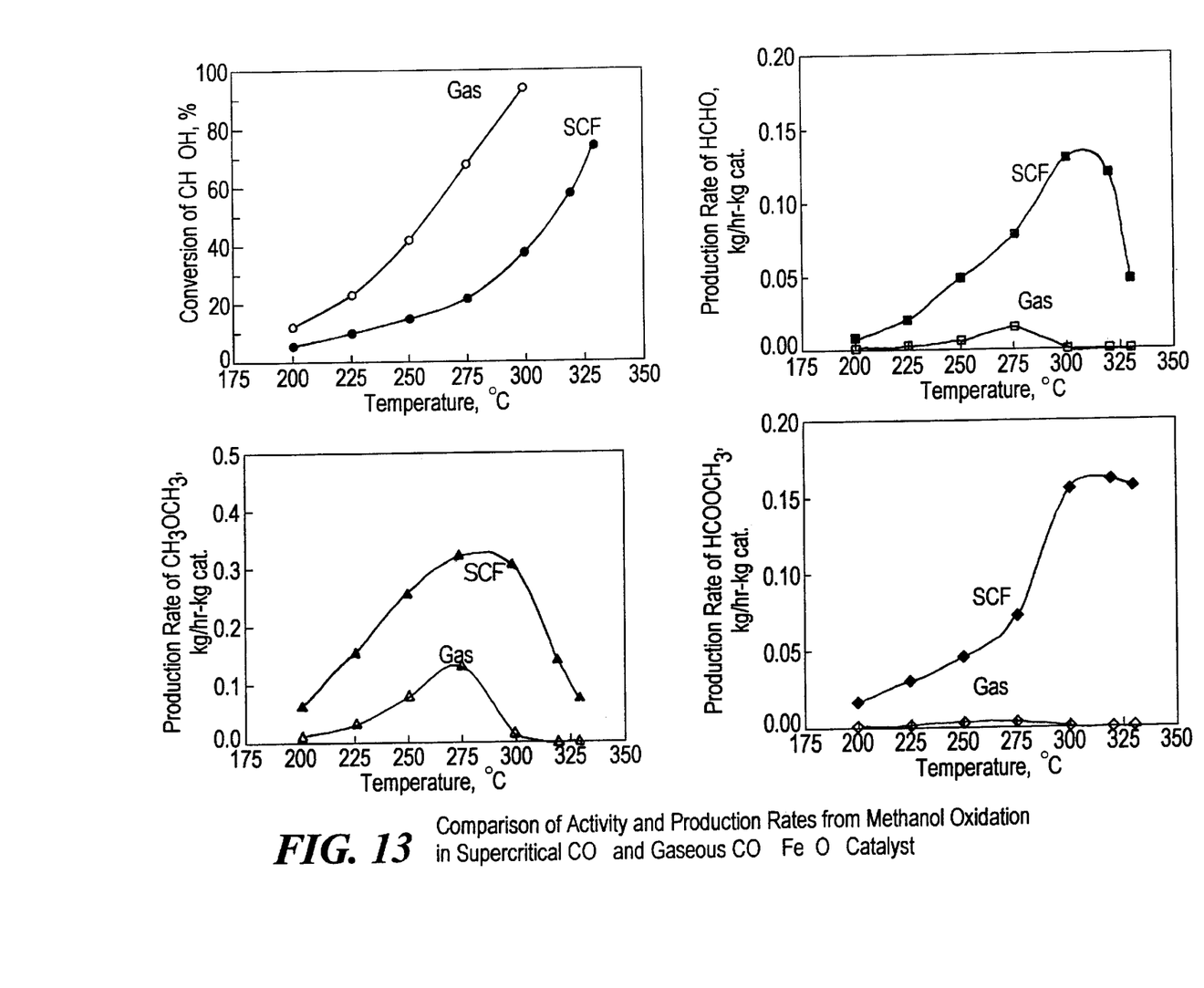

FIG. 13: Comparison of activity and production rates from partial oxidation in SCF $CO_2$ versus gaseous $CO_2$ over $Fe_2O_3$ catalyst

Several features or benefits of the invention are illustrated by this exemplary system. Referring to FIGS. 2–6, the methanol conversion profiles show good methanol conversion level at relatively mild system temperatures, e.g., 250°–280° C. As shown in FIGS. 2–4, increasing catalyst acidity (here, by increasing the iron oxide content in the catalyst) reduces the temperature for higher methanol conversion.

As can be more clearly seen in FIGS. 7–11, the catalyst acidity can be selected to determine the particular product produced. The ester (methyl formate) is the dominant product species using 1% iron oxide on silica, while at 10% iron oxide on silica results in the aldehyde (formaldehyde) as the major product, and at 20% iron oxide on silica and pure iron oxide the ether (dimethyl ether) is the dominant product.

For the illustrated methanol partial oxidation process, the following overall reactions are suggested as a theoretical explanation but not as a limitation on the claimed invention.

(4-1)

(4-2)

(4-3)

-continued (4-4)

(4-5)

FIG. 13 shows the superiority of the disclosed process in terms of the production rates of the desired products. A comparison of methanol oxidation using iron oxide catalyst in gaseous $CO_2$ versus SCF $CO_2$ (as disclosed herein) is shown. While the SCF process does not have as high a level of MeOH conversion as with the gaseous phase reaction, the production of the desired ether, aldehyde and ester is higher in the disclosed SCF process.

What is claimed is:

1. A process for partially oxidizing methanol, comprising the steps of:
   a. introducing into a reactor unit containing a bed of solid acid catalyst selected from the group consisting of $Fe_2O_3/SiO_2$, $Fe_2O_3/Al_2O_3$, and $Fe_2O_3/MoO_3$, amounts of said methanol and oxygen; and a supercritical fluid (SCF) mobile phase; and
   b. partially oxidizing said methanol to its corresponding ether, aldehyde, ester or acid, wherein the operating pressure and temperature is greater than the critical point pressure and temperature of mixture of alcohol, oxygen and SCF.

2. The process of claim 1 wherein said solid acid catalyst is an aerogel.

3. The process of claim 1 wherein said partial oxidation occurs at a pressure of from about 1200 to 1800 psig and a temperature range of about 200°–330° C.

4. The process of claim 1 wherein said solid acid catalyst is an aerogel; and the ratio of oxygen to said methanol is from about 0.6:1 to 2.5:1.

5. The process of claim l wherein the ratio of oxygen to said alcohol is from about 0.6:1 to 2.5:1.

* * * * *